United States Patent [19]

Bargiotti et al.

[11] Patent Number: 5,496,808
[45] Date of Patent: Mar. 5, 1996

[54] MONO AND BIS ALKYLAMINO-ANTHRACYCLINES

[75] Inventors: Alberto Bargiotti; Michele Caruso, both of Milan; Daniela Faiardi, Pavia; Antonino Suarato; Nicola Mongelli, both of Milan, all of Italy

[73] Assignee: Farmitalia Carlo Erba S.R.L., Milan, Italy

[21] Appl. No.: 904,650

[22] Filed: Jun. 26, 1992

[30] Foreign Application Priority Data

Jul. 5, 1991 [GB] United Kingdom ............ 9114549

[51] Int. Cl.$^6$ ............ A61K 31/70; C07H 15/24
[52] U.S. Cl. ............ 514/34; 536/6.4
[58] Field of Search ............ 536/6.4; 574/34

[56] References Cited

U.S. PATENT DOCUMENTS 4,591,637  5/1986  Acton et al. ............ 536/6.4
5,049,549  9/1991  Kolar et al. ............ 514/34

OTHER PUBLICATIONS

Chemical Abstracts, vol. 109, No. 23, AN–211398t, Dec. 5, 1988.
Journal of Medicinal Chemistry, vol. 29, 1986, pp. 2120–2122, E. M. Action, et al., "N–(2–Hydro–Xyethyl)Doxorubicin From Hydrolysis of 3'–(3–Cyano–4–Morpholinyl)Doxorubicin".

Primary Examiner—Elli Peselev
Attorney, Agent, or Firm—Oblon, Spivak, McClelland, Maier, & Neustadt

[57] ABSTRACT

An anthracycline glycoside of general formula 1:

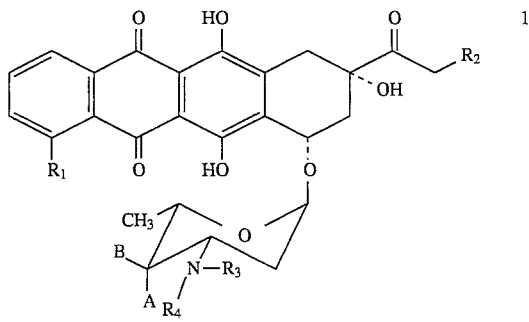

wherein $R_1$ is hydrogen or methoxy group; $R_2$ is hydrogen or hydroxy group, A and B both represent hydrogen or one of A and B is hydrogen and the other is hydroxy or a group of formula $-OSO_2R_5$ in which $R_5$ is C1–C4 alkyl or aryl optionally substituted by C1–C4 alkyl, nitro, amino, methoxy or halogen; $R_3$ is a hydrogen atom or a group of formula 2 and $R_4$ is a group of formula 2

$$-(CH_2)_n-X \qquad 2$$

in which n is 2 or 3 and X is hydroxy group, a halogen or a group of formula $-OSO_2R_5$ in which $R_5$ is as defined above and with the proviso that if $R_2$, X and A are an hydroxy group and $R_3$=H, n must be 3; or a pharmaceutically acceptable salt thereof.

Compounds of the invention have activity as antitumor agents. Processes for their preparation and pharmaceutical composition containing them are also disclosed.

6 Claims, No Drawings

MONO AND BIS ALKYLAMINO-ANTHRACYCLINES

The present invention relates to new anthracycline glycosides, to processes for their preparation and to pharmaceutical compositions containing them.

The invention provides antracyclines glycosides of general formula 1 in which the amino group of the sugar moiety bears mono or bis alkyl-substituted chains:

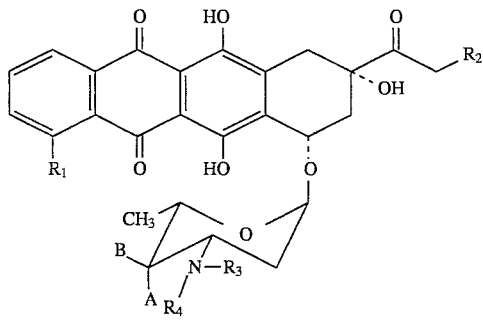

wherein $R_1$ is hydrogen or methoxy group; $R_2$ is hydrogen or hydroxy group, A and B both represent hydrogen or one of A and B is hydrogen and the other is hydroxy or a group of formula $-OSO_2R_5$ in which $R_5$ is C1–C4 alkyl or aryl optionally substituted by C1–C4 alkyl, nitro, amino, methoxy or halogen; $R_3$ is a hydrogen atom or a group of formula 2 and $R_4$ is a group of formula 2

$$-(CH_2)_n-X \qquad 2$$

in which n is 2 or 3 and X is hydroxy group, a halogen or a group of formula $-OSO_2R_5$ in which $R_5$ is as defined above and with the proviso that if $R_2$, X and A are an hydroxy group and $R_3$=H, n must be 3; or a pharmaceutically acceptable salt thereof.

Compounds of the invention exibit antitumor activity.
Example of compounds of the invention include:
1a: N-(3-hydroxypropyl)daunorubicin
 [$R_1$=OCH$_3$, $R_2$=$R_3$=H, A=OH, B=H, $R_4$=(CH$_2$)$_3$—OH]
1b: N-(3-hydroxypropyl)doxorubicin
 [$R_1$=OCH$_3$, $R_2$=OH, $R_3$=H, A=OH, B=H, $R_4$=(CH$_2$)$_3$—OH]
1c: N,N-bis(3-hydroxypropyl)daunorubicin
 [$R_1$=OCH$_3$, $R_2$=H, A=OH, B=H, $R_3$=$R_4$=(CH$_2$)$_3$—OH]
1d: 4-demethoxy-N-(2-hydroxyethyl)daunorubicin
 [$R_1$=$R_2$=$R_3$=H, A=OH, B=H, $R_4$=(CH$_2$)$_2$—OH]
1e: N,N-bis(2-hydroxyethyl)daunorubicin
 [$R_1$=OCH$_3$, $R_2$=H, A=OH, B=H, $R_3$=$R_4$=(CH$_2$)$_2$—OH]
1f: N,N-bis(2-hydroxyethyl)doxorubicin
 [$R_1$=OCH$_3$, $R_2$=OH, A=OH, B=H, $R_3$=$R_4$=(CH$_2$)$_2$—OH]
1g: 4-demethoxy-N,N-bis(2-hydroxyethyl)daunorubicin
 [$R_1$=$R_2$=H, A=OH, B=H, $R_3$=$R_4$=(CH$_2$)$_2$—OH]
1h: 4-demethoxy-4'-O-methansulfonyl-N,N-bis(2-chloroethyl)daunorubicin
 [$R_1$=$R_2$=H, A=OSO$_2$CH$_3$, B=H, $R_3$=$R_4$=(CH$_2$)$_2$—Cl]
1i: 4-demethoxy-N,N-bis(2-chloroethyl)daunorubicin
 [$R_1$=$R_2$=H, A=OH, B=H, $R_3$=$R_4$=(CH$_2$)$_2$—Cl]
1j: 4'-O-methansulfonyl-N,N-bis(2-chloroethyl)daunorubicin
 [$R_1$=OCH$_3$, $R_2$=H, A=OSO$_2$CH$_3$, B=H, $R_3$=$R_4$=(CH$_2$)$_2$—Cl]
1k: N,N-bis(2-chloroethyl)daunorubicin
 [$R_1$=OCH$_3$, $R_2$=H, A=OH, B=H, $R_3$=$R_4$=(CH$_2$)$_2$—Cl]
1l: 4'-epi-4'-O-methansulfonyl-N,N-bis(2-chloroethyl)daunorubicin
 [$R_1$=OCH$_3$, $R_2$=H, A=H, B=OSO$_2$CH$_3$, $R_3$=$R_4$=(CH$_2$)$_2$—Cl]
1m: 4'-epi-N,N-bis(2-chloroethyl)daunorubicin
 [$R_1$=OCH$_3$, $R_2$=H, A=H, B=OH, $R_3$=$R_4$=(CH$_2$)$_2$—Cl]
1n: 4-demethoxy-4'-epi-4'-O-methansulfonyl-N,N-bis(2-chloroethyl)daunorubicin
 [$R_1$=$R_2$=H, A=H, B=OSO$_2$CH$_3$, $R_3$=$R_4$=(CH$_2$)$_2$—Cl]
1o: N,N-bis(2-chloroethyl)doxorubicin
 [$R_1$=OCH$_3$, $R_2$=OH, A=OH, B=H, $R_3$=$R_4$=(CH$_2$)$_3$—Cl]
and pharmaceutically acceptable salts thereof, such as the hydrochloride salt.

The compounds of the present invention can be prepared by several methods starting from compounds of formula 3

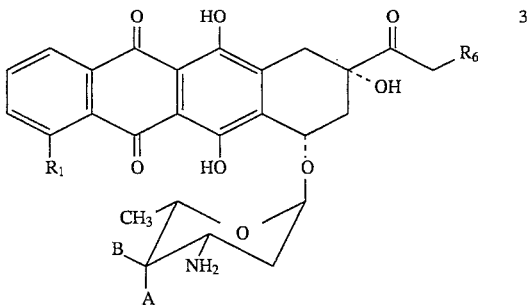

wherein $R_1$, A and B are as defined above for formula 1, $R_6$ is hydrogen, a hydroxyl group or an acidic sensitive masked group for the hydroxy group. Example of suitable protecting groups include those described in British Patent Application 9017024.2 filed Mar. 8, 1990 entitled "New Linker for Bioactive Agents".

Example of the starting compounds of formula 3 include daunorubicin [3a: $R_1$=OCH$_3$, $R_2$=H, A=OH, B=H], 4-demethoxydaunorubicin [3b: $R_1$=$R_2$=H, A=OH, B=H], doxorubicin [3c: $R_1$=OCH$_3$, $R_2$=OH, A=OH, B=H], 4-demethoxy-4'-epi-daunorubicin [3d: $R_1$=$R_2$=H, A=H, B=OH], 4'-epi-daunorubicin [3e: $R_1$=OCH$_3$, $R_2$=H, A=H, B=OH], or masked derivative of doxorubicin at C-14.

The compounds of general formula 1 can be prepared by alkylating the amino group of the sugar moiety using conventional methods. For instance, mono 2- or 3-hydroxyalkylamino derivatives, which are compounds of formula 1 as defined above wherein $R_3$ and $R_4$ are as defined above wherein X is a hydroxy group, can be prepared by a process comprising (i) reacting a compound of formula 3 as defined above, the compound of formula 3 being dissolved in a polar aprotic solvent, with an alkylating agent of general formula 4

$$X-(CH_2)_n-Hal \qquad 4$$

wherein n is 2 or 3, X is hydroxy and Hal represents an halogen; and, if desired, (ii) purifying the resulting anthracycline glycosides of formula 1 on a chromatographic column; and/or, if desired, (iii) converting the anthracycline glycoside of formula 1 into a pharmaceutically acceptable acid addition salt thereof.

Preferably the halogen in formula 4 is iodine or bromine. The polar aprotic solvent is preferably dry and is, for example, dimethylformamide or acetonitrile. The reaction is suitably conducted at a temperature from 20° to 30° C., typically for a time of from four to twenty four hours.

Bis 2- or 3-hydroxy-alkylamino derivatives, which are compounds of formula 1 as defined above wherein $R_3$ and $R_4$ are a group of formula 2 as defined above wherein X is a hydroxy group, can also be prepared by the process as described above. The reaction time for step (i) is then typically 1 to 3 weeks.

Bis 2-hydroxyethylamino compounds of general formula 1 can also be prepared by a process comprising (i) reacting a compound of formula 3 as defined above, preferably as free base, with ethylene oxide; and, if desired, (ii) purifying the resulting anthracycline glycoside of formula 1 on a chromatographic column; and/or, if desired, (iii) converting the anthracycline glycoside of formula 1 into a pharmaceutically acceptable acid addition salt thereof. Preferably the compound of formula 3 is first dissolved in a solvent comprising methanol and methylene chloride. Typically step (i) is conducted in the dark, and at a starting temperature of about −40° C. The temperature is then typically increased gradually to room temperature. Suitably it remains at room temperature for up 3 days.

Anthracycline glycosides of general formula 1 as defined above in which $R_2$ is hydrogen and one or both of $R_3$ and $R_4$ represent a group of formula $(CH_2)_n$—$OSO_2R_5$, as defined above, can be prepared by a process comprising treating the corresponding mono or bis-hydroxyamino derivatives of formula 1 with a sulfonyl chloride of formula 5

$$Cl\text{—}SO_2R_5 \qquad 5$$

wherein $R_5$ is a residue as defined above; and, if desired, (ii) purifying the resulting anthracyline glycoside of formula 1 on a chromatographic column. Typically step (i) is conducted in an aprotic solvent, such as methylene chloride. Suitably it is conducted in the presence of a tertiary amine, such as trietylamine or pyridine.

It is also possible to prepare anthracycline glycoside derivatives of general formula 1 in which $R_2$ is a hydroxy group from the corresponding mono or bis-hydroxyamino compounds of formula 1 in which the C-14 hydroxy group, $R_2$=OH is masked with an acid sensitive protecting group. Mild acidic treatment of the latter produces the desired sulfonylalkylamino anthracycline.

Compounds of general formula 1 in which X is a halogen can be prepared by a process comprising (i) dissolving an anthracycline glycoside of formula 1 as defined above, wherein one or both of $R_3$ and $R_4$ is a group of formula $OSO_2R_5$ wherein $R_5$ is alkyl or aryl group, in an aprotic solvent and reacting the resulting solution with a corresponding halide salt; and, if desired, (ii) purifying the resulting anthracycline glycoside on a chromatographic column; and/or, if desired, (iii) isolating the desired compound as the corresponding hydrohalide. When X is chlorine, the corresponding chlorine salt may be, for example, pyridinium chloride. The aprotic solvent is, for example, acetone. The reaction is preferably conducted at room temperature.

Anthracycline glycosides of general formula 1 as defined above in which X is chlorine, $R_2$ is hydrogen, both A and B represent hydrogen or one of A or B represent the group —$OSO_2R_5$ wherein $R_5$ is as defined above can be prepared by a process comprising (i) treating the corresponding mono or bis-hydroxyalkyl amino derivative of formula 1 as defined above in dry pyridine with sulfonyl chloride of formula 5; and, if desired (ii) purifying the resulting anthracycline glycoside on a chromatographic column; and/or, if desired, (iii) isolating the desired compound as the corresponding hydrohalide. Typically step (i) is conducted in the dark, and at a temperature of 0° C. under nitrogen. Suitably, it remains at 0° C. fou up 16 hrs.

It is also possible to prepare anthracycline glycoside derivatives of general formula 1 in which $R_2$ is a hydroxy group from the corresponding mono or bis-hydroxyalkyl amino compounds of formula 1 in which the C-14 hydroxy group, $R_2$=OH, is masked with an acid sensitive protecting group. Mild acidic treatment of the latter produces the desired chloroalkyl amino anthracycline derivative.

The compounds of the invention have activity as antitumor agents. A mammal, for example a human, can therefore be treated by a method comprising administrating thereto, by an oral or parenteral route, a pharmaceutically effective amount of an anthracycline glycoside of formula 1 as defined above or a pharmaceutically acceptable acid addition salt thereof.

The invention also provides a pharmaceutical composition comprising a pharmaceutically acceptable diluent or carrier and, as an active principle, an anthracycline glycoside of formula 1, or a pharmaceutically acceptable salt thereof. Conventional carriers or diluents may be used. The composition may be formulated and administred, for example intravenously, in conventional manner.

The following Examples illustrate the invention without limiting it.

EXAMPLE 1

Preparation of: N-(3-hydroxypropyl)daunorubicin
[$R_1$=OCH$_3$, $R_2$=$R_3$=H, A=OH, B=H,
$R_4$=(CH$_2$)$_3$—OH] (1a)

To a solution of daunorubicin (3a) (0.2 g, 0.38 mmol) in anhydrous dimethylformamide (2 ml) was added 3-bromo-1-propanol [4: X=OH, Hal=Br, n=3] (200 μl, 2.16 mmol) at room temperature under nitrogen and stirring was continued for five days. After that the solvent was removed in vacuo; the crude oil was dissolved in methylene chloride (10 ml) and trifluoroacetic anhydride (425 μl, 3 mmol) added. The mixture was stirred for one hour at 0° C. then poured into satured aqueous sodium hydrogen carbonate and extracted with methylene chloride. The combined organic extracts were washed with water and the organic solvent was removed under reduced pressure. The crude oil was dissolved in methanol (50 ml) and stirred for one hour at 40° C., concentrated to small volume and purified by flash chromatography on silicic acid column using as eluting system a mixture of methanol and methylene chloride (10/90 by volume) to give after treatment with methanolic anhydrous hydrochloric acid the title compound 1a (0.12 g, yield 54%) as hydrochloride salt.

TLC on Kieselgel Plate F$_{254}$ (Merck), eluting system: methylene chloride, methanol, acetic acid, water (80:20:7:3 by volume) R$_f$=0.42

FD-MS: m/e 569 (M$^+$)

$^1$HNMR (200 MHz, DMSO d$_6$) δ: 1.16 (d, J=6.4 Hz, 3H, CH$_3$-5'); 1.5–1.8 (m, 4H, CH$_2$CH$_2$, CH$_2$-2') 2.15 (m, 2H, CH$_2$-8); 2.25 (s, 3H, COCH$^3$); (2.6–2.9 (m, 2H, CH$_2$NH); 2.99, 2.89 (ABq, J=18.0 Hz, 2H, CH$_2$-10); 3.31 (m, 1H, H-3'); 3.41 (m, 2H, CH$_2$—OH); 3.63 (m, 1H, H-4'); 3.92 (s, 3H, OCH$_3$); 4.14 (q, J=6.4 Hz, 1H, H-5'); 4.96 (m, 1H, H-7); 5.29 (m, 1H, H-1'); 5.49 (s, 1H, OH-9); 7.6–7.9 (m, 3H, aromatic H's ).

EXAMPLE 2

Preparation of:
N,N-bis(3-hydroxypropyl)daunorubicin
[$R_1$=OCH$_3$, $R_2$=OH, A=OH, B=H,
$R_3$=$R_4$=(CH$_2$)$_3$—OH] (1c)

The title compound was prepared by keeping daunorubicin (3a) (0.2 g, 0.38 mmol) and 3-bromo-1-propanol (200 µl, 2.16 mmol) in anhydrous dimethylformamide for three weeks under nitrogen. After that the solvent was removed in vacuo and the crude oil was purified by flash chromatography on silicic acid column using as eluting system a mixture of methanol and methylene chloride (10/90 by volume) to give after treatment with methanolic anhydrous hydrochloric acid N,N-bis(3-hydroxypropyl)daunorubicin (1c) (0.10 g, yield 50%) as hydrochloride salt.

TLC on Kieselgel Plate $F_{254}$ (Merck), eluting system: methylene chloride, methanol, acetic acid, water (30:4:1:0.5 by volume) $R_f$=0.14

FD-MS: m/e 627 (M$^+$)

$^1$HNMR (200 MHz, CDCl$_3$) δ: 1.29 (d, J=6.4 Hz, 3H, C$\underline{H}_3$-5'); 1.8–1.5 (m, 5H, 2xNHCH$_2$C$\underline{H}_2$, $\underline{H}$-2'eq); 2.04 (m, 1H, $\underline{H}$-2'ax); 2.09 (m, 1H, $\underline{H}$-8ax); 2.34 (m, 1H, $\underline{H}$-8eq); 2.41 (s, 3H, COC$\underline{H}_3$); 2.5–2.9 (m, 5H, 2xNHC$\underline{H}_2$, $\underline{H}$-3'); 2.95 (d, J=19.0 Hz, 1H, $\underline{H}$-10ax); 3.21 (dd, J=1.5, 19.0 Hz, 1H, $\underline{H}$-10eq); 3.8–3.6 (m, 5H, 2xC$\underline{H}_2$OH, $\underline{H}$-4'); 4.07 (s, 3H, OC$\underline{H}_3$); 4.09 (q, J=6.4 Hz, 1H, $\underline{H}$-5'); 5.29 (m, 1H, $\underline{H}$-7); 5.57 (d, J=3.3 Hz, 1H, $\underline{H}$-1'); 7.38 (d, J=8.4 Hz, 1H, $\underline{H}$-3); 7.77 (dd, J=7.4, 8.4 Hz, 1H, $\underline{H}$-2); 8.01 (d, J=7.4 Hz, 1H, $\underline{H}$-1); 14.0, 13.3 (broad signals, 2H, 2xphenolic —OH).

EXAMPLE 3

Preparation of: N,N-bis(2-hydroxyethyl)doxorubicin
[$R_1$=OCH$_3$, $R_2$=OH, A=OH, B=H,
$R_3$=$R_4$=(CH$_2$)$_2$—OH] (1f)

A mixture of doxorubicin (3c) (0.15 g, 0.258 mmole), methanol and methylene chloride (25 ml, 1:1 by volume) was poured in a well stopped round bottomed flask, cooled at −40° C. and added with ethylene oxide (15 ml). The reaction mixture was slowly brought at room temperature and kept for two days in the dark. After that, the solvents were removed under reduced pressure and the residue purified by flash chromatography on silicic acid column using as eluting system a mixture of methylene chloride and methanol (80:20 by volume). The title compound 1f (0.1 g, yield 60%) was converted into hydrochloride salt by treatment with methanolic anhydrous hydrochloric acid.

TLC on Kieselgel Plate $F_{254}$ (Merck), eluting system: methylene chloride, methanol, acetic acid, water (80:20:7:3 by volume) $R_f$=0.36.

FD-MS: m/e 631 (M$^+$)

$^1$HNMR (200 MHz, DMSO d$_6$) δ: 1.13 (d, J=6.6 Hz, 3H, C$\underline{H}_3$-5'); 1.53 (m, 1H, $\underline{H}$-2'eq); 1.94 (m, 1H, $\underline{H}$-2'ax); 2.16 (m, 2H, C$\underline{H}_2$-8); 2.65 (m, 4H, N(C$\underline{H}_2$CH$_2$OH)$_2$); 2.82 (m, 1H, $\underline{H}$-3'); 2.98 (m, 2H, C$\underline{H}_2$-10); 3.33 (m, 4H, N(CH$_2$C$\underline{H}_2$OH)$_2$); 3.57 (m, 1H, $\underline{H}$-4'); 4.00 (s, 3H, OC$\underline{H}_3$-4); 4.02 (dq, J=<2, 6.6 Hz, 1H, $\underline{H}$-5'); 4.35 (bm, 3H, O$\underline{H}$-4', N(CH$_2$CH$_2$O$\underline{H}$)$_2$); 4.56 (m, 2H, C$\underline{H}_2$-14); 4.84 (t, J=6.2 Hz, 1H, O$\underline{H}$-14); 4.98 (m, 1H, $\underline{H}$-7); 5.30 (m, 1H, $\underline{H}$-1'); 5.40 (s, 1H, O$\underline{H}$-9); 7.67 (m, 1H, $\underline{H}$-2); 7.93 (m, 2H, $\underline{H}$-1, $\underline{H}$-3); 13.28 (bs, 1H, O$\underline{H}$-11); 14.06 (s, 1H, O$\underline{H}$-6).

EXAMPLE 4

Preparation of:
4-demethoxy-N,N-bis(2-hydroxyethyl)daunorubicin
[$R_1$=$R_2$=H, A=OH, B=H,
$R_3$=$R_4$=(CH$_2$)$_2$—OH] (1g)

Free base 4-demethoxydaunorubicin (3b) (0.23 g, 0.5 mmol) was converted into the title compound 1 g following the procedure described in Example 3. Yield: 0.15 g as hydrochloride salt after treatment with methanolic anhydrous hydrochloric acid.

TLC on Kieselgel Plate $F_{254}$ (Merck), eluting system: methylene chloride, methanol, acetic acid, water (80:20:7:3 by volume) $R_f$=0.38.

FD-MS: m/e 585 (M$^+$)

$^1$HNMR (200 MHz, DMSO d$_6$) δ: 1.13 (d, J=6.6 Hz, 3H, C$\underline{H}_3$-5'); 1.55 (m, 1H, $\underline{H}$-2'eq); 1.93 (m, 1H, $\underline{H}$-2'ax); 2.17 (m, 2H, C$\underline{H}_2$-8); 2.26 (s, 3H, COCH$_3$); 2.65 [m, 4H, N(C$\underline{H}_2$CH$_2$OH)$_2$]; 2.82 (m, 1H, $\underline{H}$-3'); 2.99 (m, 2H, C$\underline{H}_2$-10); 3.30 [m, 4H, N(CH$_2$C$\underline{H}_2$OH)$_2$]; 3.59 (m, 1H, $\underline{H}$-4'); 4.06 (dq, J=<2, 6.6 Hz, 1H, $\underline{H}$-5'); 4.35 [bm, 3H, O$\underline{H}$-4', N(CH$_2$CH$_2$O$\underline{H}$)$_2$]; 4.96 (m, 1H, $\underline{H}$-7); 5.30 (m, 1H, O$\underline{H}$-9); 8.00 (m, 2H, $\underline{H}$-2, $\underline{H}$-3); 8.30 (m, 2H, $\underline{H}$-1, $\underline{H}$-4); 13.35 (s, 1H, O$\underline{H}$-11); 13.55 (s, O$\underline{H}$-6).

EXAMPLE 5

Preparation of
N,N-bis(2-hydroxyethyl)daunorubicin [$R_1$=OCH$_3$,
$R_2$=H, A=OH, B=H, $R_3$=$R_4$=(CH$_2$)$_2$—OH]
(1e)

The title compound 1e was prepared from daunorubicin (3a) following the same procedure described in Example 4.

TLC on Kieselgel Plate $F_{254}$ (Merck), eluting system: methylene chloride, methanol, acetic acid, water (80:20:7:3 by volume) $R_f$=0.28

FD-MS: m/e 615 (M$^+$)

EXAMPLE 6

Preparation of 4-demethoxy-4'-O-methansulfonyl-N,
N-bis(2-chloroethyl)daunorubicin

[$R_1$=$R_2$=H, A=OSO$_2$CH$_3$, B=H, $R_3$=$R_4$=(CH$_2$)$_2$—Cl] (1h)

4-demethoxy-N,N-bis(2-hydroxyethyl)daunorubicin (1 g) (0.3 g, 0.5 mmol) prepared as described in Example 4, was dissolved with dry pyridine (15 ml) cooled at 0° C. and added with methansulfonyl chloride (1 ml) and kept overnight at 0° C. under stirring with a nitrogen blanket. After that, the reaction mixture was poured into water/ice and extracted with methylene chloride. The organic layer was washed with cold water, dried over anhydrous sodium sulphate, and concentrated under reduced pressure. The crude material was purified by flash chromatography on silicic acid column using as eluting system a mixture of methylene chloride and acetone (97:3 by volume) to give the title compound 1h (0.1 g, yield 30%).

TLC on Kieselgel Plate $F_{254}$ (Merck), eluting system: methylene chloride, acetone (20:1 by volume) $R_f$=0.48.

FD-MS: m/e 680 (M$^+$)

$^1$HNMR (200 MHz, CDCl$_3$) δ: 1.35 (d, J=6.5 Hz, 3H, C$\underline{H}_3$-5'); 1.8–2.4 (m, 4H, $\underline{H}$-2'eq, $\underline{H}$-2'ax, $\underline{H}$-8ax, $\underline{H}$-8eq); 2.42 (s, 3H, C$\underline{H}_3$—CO); 3.06 (t, 4H, J=7.1 Hz, C$\underline{H}_2$—N—

CH$_2$); 3.17 (m, 1H, H-3'); 3.43 (m, 4H, 2xCH$_2$-Cl); 4.16 (m, 1H, H-5'); 4.40 (s, 1H, OH-9); 4.91 (s, 1H, H-4'); 5.30 (dd, J=2.1, 3.7 Hz, 1H, H-7); 5.60 (d, 1H, J=3.4 Hz, H-1'); 7.85 (m, 2H, H-2, H-3); 8.37 (m, 2H, H-1, H-4); 13.55 (s, 1H, OH-11); 13.64 (s, 1H, OH-6).

EXAMPLE 7

Biological Assays 4-demethoxy-4'-O-methansulfonyl-N,N-bis(2-chloroethyl)daunorubicin (compound 1h) was tested "in vitro" as inhibitor of colony growth on two human cell lines: LoVo (colon adenocarcinama) and LoVo/DX (colon adenocarcinoma resistant to Doxorubicin) in comparison with 4-demethoxydaunorubicin (3b) and Doxorubicin (3c) (Table 1). When compared with 4-demethoxydaunorubicin and Doxorubicin a striking higher activity on the doxorubicin-resistant cell line was observed for compound 1h.

Compound 1h was also evaluated "in vivo" against P388 murine Leukemias, sensitive (Table 2) and resistant to Doxorubicin (Johnson). When tested on resistant Leukemia, compound 1h showed high activity (Table 3).

TABLE 1

"in vitro" cytotoxic activity.

| Compounds | Cytotoxicity (IC$_{50}$ = ng/ml)[1] | | |
|---|---|---|---|
| | LoVo | LoVo/DX | R.I.[2] |
| 1h | 4.3 | 14.0 | 3.3 |
| 4-demethoxy-daunorubicin | 4.0 | 48.0 | 12.0 |
| Doxorubicin | 82.5 | 4975 | 60.3 |

Colony assay: 4 hr treatment
[1]IC$_{50}$ = concentration inhibiting 50% of colony formation
[2]R.I. = Resistance Index = (IC$_{50}$ LoVo/DX)(IC$_{50}$ LoVo)

TABLE 2

Antitumor Activity Against Ascitic P388 Leukemia[3]

| Compounds | Dose[4] (mg/kg) | T/C[5] % | TOX[6] |
|---|---|---|---|
| 1h | 1.0 | 184 | 0/12 |
| | 1.4 | 217 | 0/6 |
| | 2.0 | 233 | 1/6 |
| | 2.8 | 78 | 6/6 |
| 4-demethoxy-daunorubicin | 0.33 | 142 | 0/27 |
| | 0.5 | 160 | 0/28 |
| | 0.75 | 163 | 4/28 |
| Doxorubicin | 10.0 | 299 | 0/10 |
| | 15.0 | 90 | 3/6 |

[3]10$^6$ cell/mouse were injected i.p. on day 0.
[4]Compounds were suspended in Tween 80 10% and injected i.p. one day after tumor transplantation.
[5]Median survival time of treated mice/Median survival time of controls × 100.
[6]No. of toxic deaths/total No. of mice.

TABLE 3

Antitumor Activity Against Disseminated P388/DX Johnson Leukemia[7]

| Compounds | Dose[4] (mg/kg) | T/C[5] % | TOX[6] |
|---|---|---|---|
| 1h | 1.2 | 133 | 0/6 |
| | 1.6 | 144 | 0/6 |

TABLE 3-continued

Antitumor Activity Against Disseminated P388/DX Johnson Leukemia[7]

| Compounds | Dose[4] (mg/kg) | T/C[5] % | TOX[6] |
|---|---|---|---|
| | 2.1 | 185 | 0/6 |
| | 2.8 | 220 | 0/6 |
| | 3.7 | 250 | 0/6 |
| 4-demethoxy-daunorubicin | 1.9 | 106 | 0/10 |
| | 2.5 | 89 | 0/10 |
| Doxorubicin | 16.9 | 106 | 0/6 |
| | 22.0 | 94 | 3/6 |

[7]10$^5$ cell/mouse were injected i.v. on day 0.
[4]Compounds were suspended in Tween 80 10% and injected i.p. one day after tumor transplantation.
[5]Median survival time of treated mice/Median survival time of controls × 100.
[6]No. of toxic deaths/total No. of mice.

We claim:

1. An anthracycline glycoside of formula 1:

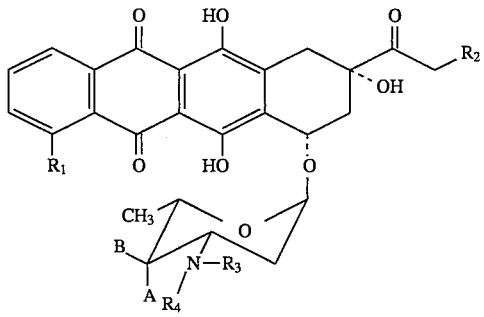

wherein R$_1$ is hydrogen or methoxy group; R$_2$ is hydrogen or hydroxy group, A and B both represent hydrogen or one of A and B is hydrogen and the other is hydroxy or a group of formula —OSO$_2$R$_5$ in which R$_5$ is C1–C4 alkyl; R$_3$ is a hydrogen atom or a group of formula 2 and R$_4$ is a group of formula 2

$$—(CH_2)_n—X \qquad 2$$

in which n is 2 or 3 and X is a halogen or a group of formula —OSO$_2$R$_5$ in which R$_5$ is as defined above; or a pharmaceutically acceptable salt thereof.

2. A compound according to claim 1 wherein, in formula 2, X is chlorine.

3. A compound according to claim 1 wherein the pharmaceutically acceptable salt is a hydrochloride salt.

4. A compound according to claim 1 which is a member selected from the group consisting of 4-demethoxy-4'-O-methanesulfonyl-N,N-bis(2-chloroethyl)-daunorubicin, 4-demethoxy-N,N-bis(2-chloroethyl)daunorubicin, 4'-O-methanesulfonyl-N,N-bis(2-chloroethyl)daunorubicin, N,N-bis(2-chloroethyl)daunorubicin, 4'-epi-4'-O-methanesulfonyl-N,N-bis(2-chloroethyl)daunorubicin, 4'-epi-N,N-bis(2-chloroethyl)daunorubicin, 4-demethoxy-4'-epi-4'-O-methanesulfonyl-N,N-bis(2-chloroethyl)daunorubicin, N,N-bis(2-chloroethyl)doxorubicin and pharmaceutically acceptable salts thereof.

5. An antitumor composition comprising an effective amount of an anthracycline glycoside of Formula 1 or a pharmaceutically acceptable salt thereof as defined in claim 1 and a pharmaceutically acceptable diluent or carrier.

6. A method for treatment of tumors in subjects in need thereof, comprising administering thereto an effective amount of the composition of claim 5.

* * * * *